Figure 1:
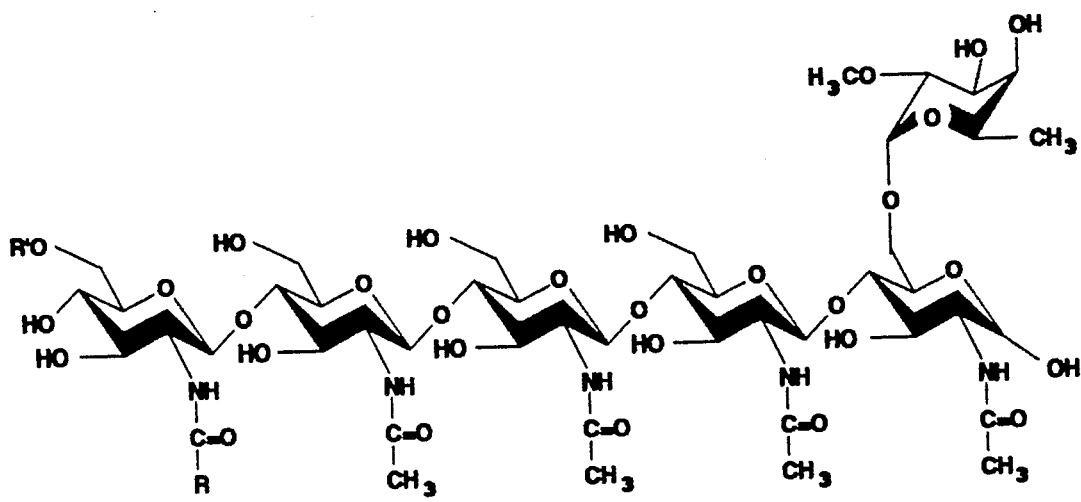

United States Patent [19]

Stacey et al.

[11] Patent Number: 5,321,011
[45] Date of Patent: * Jun. 14, 1994

[54] PENTASACCHARIDE PHYTOHORMONES AND METHODS FOR THEIR USE

[75] Inventors: Gary Stacey, Knoxville, Tenn.; Russell W. Carlson, Athens, Ga.; Herman Spaink, Leiden, Netherlands

[73] Assignee: The University of Tennessee Research Corporation, Knoxville, Tenn.

[*] Notice: The portion of the term of this patent subsequent to Dec. 29, 2009 has been disclaimed.

[21] Appl. No.: 822,925

[22] Filed: Jan. 21, 1992

Related U.S. Application Data

[63] Continuation-in-part of Ser. No. 771,356, Oct. 4, 1991, Pat. No. 5,175,149.

[51] Int. Cl.$^5$ .................. A61K 31/70; C07H 5/06; C07H 13/06
[52] U.S. Cl. ..................... 514/23; 514/25; 514/54; 514/55; 514/62; 536/53; 536/55.1; 536/55.2; 71/7
[58] Field of Search ............ 536/53, 55.1, 55.2; 47/57.6; 514/23, 25, 54, 55, 62; 71/7

[56] References Cited

U.S. PATENT DOCUMENTS

| | | | |
|---|---|---|---|
| 2,200,532 | 5/1940 | Bond | 71/7 |
| 4,077,793 | 3/1978 | Krupicka | 71/7 |
| 4,223,023 | 9/1980 | Furda | 536/20 |
| 4,711,656 | 12/1987 | Kaneshiro | 71/7 |
| 4,720,461 | 1/1988 | Urban | 435/878 |
| 4,812,159 | 3/1989 | Freepons | 47/57.6 |
| 4,863,866 | 9/1989 | Zablotowicz et al. | 435/252 |
| 4,878,936 | 11/1989 | Handelsman et al. | 71/7 |
| 4,966,847 | 10/1990 | Stacey et al. | 435/172 |
| 4,983,519 | 1/1991 | Stacey et al. | 435/172.3 |
| 5,001,061 | 3/1991 | Rolfe et al. | 435/172.3 |
| 5,008,194 | 4/1991 | Rolfe et al. | 435/172.3 |
| 5,021,076 | 6/1991 | Kuykendall et al. | 71/7 |
| 5,023,180 | 6/1991 | Appelbaum et al. | 435/172.3 |
| 5,175,149 | 12/1992 | Stacey et al. | 514/23 |

OTHER PUBLICATIONS

Coutts, R. T. et al., *Polysaccharides, Peptides and Proteins*, pp. 60–62, 1966.

Dazzo, F. B. et al., "*Rhizobium* Lipopolysaccharide Modulates Infection Thread Development in White Clover Root Hairs" *J. Bacteriology*, v. 173, No. 17, pp. 5371–5384, 1991.

Primary Examiner—Johnnie R. Brown
Assistant Examiner—Anita Varma
Attorney, Agent, or Firm—Luedeka, Neely & Graham

[57] ABSTRACT

A phytohormone for inducing root hair curling and root nodulation in the roots of leguminous plants particularly in the absence of nitrogen-fixing bacteria. The phytohormone comprises a pentasaccharide having a fatty acid condensed on the non-reducing end. A method for treating the roots of leguminous plants for inducing root hair curling and root nodulation is also disclosed.

6 Claims, 1 Drawing Sheet

| Compound | R | R' | m + n |
|---|---|---|---|
| BJ Nod-V (C18:1) | (CH$_2$)$_7$-CH=CH-(CH$_2$)$_7$CH$_3$ | H | — |
| BJ Nod-V (Ac, C18:1) | (CH$_2$)$_7$-CH=CH-(CH$_2$)$_7$CH$_3$ | CH$_3$CH$_2$C(=O) | — |
| BJ Nod-V (C16:0) | (CH$_2$)$_{15}$CH$_3$ | H | — |
| BJ Nod-V (Ac, C16:0) | (CH$_2$)$_{15}$CH$_3$ | CH$_3$CH$_2$C(=O) | — |
| BJ Nod-V (C16:1) | (CH$_2$)$_m$-CH=CH-(CH$_2$)$_n$-CH$_3$ | H | 13 |

PENTASACCHARIDE PHYTOHORMONES AND METHODS FOR THEIR USE

This is a continuation-in-part of application Ser. No. 07/771,356, filed Oct. 4, 1991, now U.S. Pat. No. 5,175,149, issued Dec. 29, 1992.

The present invention relates to compounds and compositions for inducing changes in plants. The present invention also relates to methods for the application of those compounds and compositions to plants.

Phytohormones are compounds which induce changes in plants. Such compounds are useful in the communication between plants and other organisms. For example, many species of plants produce a phytohormone which is released from their roots into the soil. The hormone prevents the roots of plants of the same species from growing in that area. Therefore, plants of the same species in a limited area will have root systems that do not overlap.

Phytohormones are also released by organisms other than plants. Nitrogen-fixing bacteria, such as Rhizobium, Bradyrhizobium, and Azorhizobium species, release hormones in the vicinity of the roots of leguminous plants, such as soybean or alfalfa. Such hormones induce nodulation and root hair curling in the plants which make the plant roots suitable for symbiotic inhabitation by the bacteria. The bacteria and the plants then exist in a symbiotic relationship with the bacteria fixing nitrogen into the soil and the plants providing food to the bacteria.

Generally, the nitrogen-fixing bacteria produce the root hair curling and root nodulation phytohormone in response to the production of flavonoids by the plants. Flavonoids comprise a large group of secondary products found in all higher plants. It is believed that flavonoids induce the expression of genes in the bacteria necessary to produce the phytohormone. The proteins believed to be involved in phytohormone production are encoded by the nod and nol genes. The phytohormone is then secreted and the plants respond with the production of nodules and curled root hairs.

In order to promote the effective inoculation of leguminous plants with specific strains of rhizobial bacteria, those strains are presently coated on the seeds or introduced into the soil of the plants. Soybean farmers sow seeds which are coated with those rhizobial strains which are known to be effective nitrogen-fixers. The soil may also be pretreated with the bacteria prior to sowing. In either case, the soybean seedlings rely solely on the ability of the particular strain of bacterium to induce root hair curling and root nodulation.

Although this process is more effective than natural processes for the inoculation of the plant, the rhizobial bacteria will often be insufficient to induce the desired level of nodulation. The desired particular strains of bacteria may be partially or totally supplanted by the natural rhizobial species in the soil or the desired strains may not be particularly efficient at inducing the production of nodules for the bacteria to inhabit. The mere coating of the leguminous seeds or sowing of the soil with the desired bacterial strains does not necessarily lead to the desired inoculation of the plant. Therefore, it is desirable to have a means for inducing nodulation on the roots of leguminous plants that is independent of the presence of rhizobial bacteria.

It has not been possible previously to induce root hair curling and root nodulation in leguminous plants in the absence of nitrogen-fixing bacteria. The present inventors have discovered and purified a phytohormone which is capable of inducing root hair curling and root nodulation in the roots of leguminous plants. The phytohormone is a pentasaccharide of N-acetylglucosamine having a fatty acid condensed on the non-reducing end. The phytohormone of the present invention has the structure:

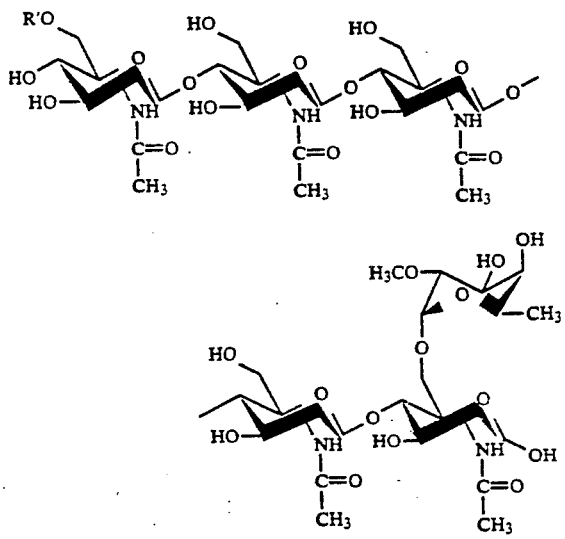

In the pentasaccharide, R is a fatty acid condensate and R' is selected from the group consisting of H and an acetyl, $CH_3CH_2C=O$. The fatty acid is selected from the group consisting of $(CH_2)_{15}-CH_3$, $(CH_2)_8-CH=CH-(CH_2)_7-CH_3$, and $(CH_2)_n-CH=CH-(CH_2)_m-CH_3$, where $n+m$ is 13. These fatty acids are alternatively designated using the terms C16:0, C18:1 and C16:1.

In accordance with the method of the present invention root hair curling and root nodulation of the roots of leguminous plants are induced. The method comprises treating the roots of the plant with a pentasaccharide phytohormone having a fatty acid condensed on the non-reducing end. The pentasaccharide has the structure shown herein above and is applied to the plant root in a concentration of from about $10^{-12}M$ to about $10^{-3}M$. At concentrations greater than about $10^{-3}M$ the hormone actually inhibits root hair curling and root nodulation. Thus, care must be taken when treating the roots of the selected leguminous plant with the phytohormone.

A drawing of the phytohormone is shown in FIG. 1. The depicted phytohormone is a pentasaccharide of N-acetylglucosamine. The non-reducing end of the pentasaccharide is substituted with a C18:1, C16:1, or C16:0 fatty acid. Further, the non-reducing sugar may be acetylated. The reducing end of the pentasaccharide is substituted with an α-2-0-methylfucose moiety at the 6-position of the reducing sugar.

The phytohormone is named as follows: "BJ" indicates that the compound is isolated from *Bradyrhizobium japonicum*; "Nod" indicates that the compound is involved in nodulation; "—V" indicates that there are five N-acetylglucosamines in the compound structure. The terms in the parentheses indicate whether the compound is acetylated ("Ac") or not at the R' position and the structure of the fatty acid at the R position. The term C18:1 indicates an 18 carbon chain with one double bond; C16:0 indicates a 16 carbon chain with no double bond; and C16:1 indicates a 16 carbon chain with one double bond. Thus, the phytohormone BJ Nod-V (Ac, C18:1) is a nodulating pentasaccharide derived from *B. japonicum* which has been acetylated and contains an 18 carbon fatty acid residue with one double bond.

The phytohormone preferably is purified by recovery from *Bradyrhizobium japonicum* which has been induced to produce the phytohormone by the presence of flavonoids. The crude extracts of the bacteria are purified by silica gel chromatography and HPLC. The purified and crude extracts were applied to leguminous plants to demonstrate their effectiveness.

In order to facilitate a better understanding of the present invention, the following examples are given primarily for the purposes of illustrating certain more specific details thereof.

PROCEDURE I

Purification of the Phytohormone

A. Preparation of soybean seed extracts (SSE): Soybean seeds (*Glycine max* cv. Essex) were rinsed with distilled water, soaked in ethanol:water mix (50:50 V/V; 1 mL per seed) and placed in a shaker incubator at 30° C. overnight. The seed extracts were then cleared by filtration through a 6 mm pore filter (Millipore) and tenfold concentrated by rotary evaporation. The concentrated soybean seed extracts (SSE) were sterilized by filtration through a 0.25 μm pore filter (Millipore) and kept frozen at −20° C. until use.

B. Preparation of *B. japonicum* extracts: Cells of *B. japonicum*, strains USDA110 or USDA135, were grown in 500 mL of minimal medium (Bergensen's MM) with glycerol as carbon source to late stationary phase (O.D.$_{600}$ of about 1.0) in a shaker incubator at 30° C. This culture was used to inoculate 5×1 L of minimal medium of 4 L flasks to an O.D.$_{600}$ from about 0.05 to about 0.08. The cultures were grown for 4–6 hours with shaking at 30° C. The SSE was diluted with distilled water to a concentration wherein 1 L of solution contained the extract of 100 soybean seeds. The diluted SSE was added (10 mL of SSE per L of culture) to the culture. Incubation was continued for 40 hours. Alternatively, the phytohormone was induced in the *B. japonicum* culture by the addition of genistein (preferably, at a concentration of 2 μm). Genistein, daidzein and their glycosylated derivatives have been shown to be active nod gene inducing flavonoids in SSE. The entire culture, or alternatively the supernatant, was extracted with 0.3 volumes of n-butanol (Mallinckrodt, n-butyl alcohol, nanograde) by shaking at 30° C. for 3 hours. The butanol and water phases were allowed to separate by standing overnight at room temperature. The butanol was then collected and the extract concentrated to dryness by rotary evaporation. The dried extract containing the phytohormone was resuspended in acetonitrile:water (50:50 V/V) and stored at room temperature until use.

C. Silica gel chromatography purification: A chromatography column (Pharmacia, C-column, 1.6×100 cm) was filled with silica gel with a particle size between 0.63 and 0.2 mm (EM Science, Silica Gel 60) prepared with acetonitrile:water (60:40 V/V). The column was washed successively with 200 mL of 82% acetonitrile, 60% acetonitrile and 82% acetonitrile. The sample was prepared by bringing the acetonitrile from 50% to 82% and then running the sample through the column. When all of the samples had been entered on the column, the column was washed with 500 mL of 82% acetonitrile. The sample was eluted in 60% acetonitrile at a flow rate of about 1.5 mL per minute. Fractions were collected and further purified by HPLC.

D. HPLC purification: The fractions from the silica gel purification were applied to a binary solvent HPLC system (two Waters MODEL 501 HPLC pumps controlled by a Waters BASELINE 810 chromatography workstation with an installed computer, Model APC IV by NEC; a 4×250 mm HPLC column, Pharmacia-LKB PEP-S C2/C18, with a guard column; detection at 206 nm with a tunable absorbance detector, Waters MODEL 484). The phytohormone was purified by four successive passes through the HPLC system. For the first pass, the HPLC system was programmed to supply 20% acetonitrile in water for the first 5 minutes, go to 40% acetonitrile in water in 10 minutes, remain at 40% acetonitrile in water for 25 minutes, and then go to 60% acetonitrile in water in 5 minutes. The total duration of the program was 45 minutes with the phytohormone eluting at about 30 minutes. For the second pass, the HPLC system was programmed to supply 20% acetonitrile in water for the first 5 minutes, go to 42% acetonitrile in water in 5 minutes, remain at 42% acetonitrile in water for 20 minutes, and then go to 60% acetonitrile in water in 5 minutes. The total duration of the program was 35 minutes with the phytohormone eluting at about 21 minutes. For the third pass, the HPLC system was programmed to supply 20% acetonitrile in water for the first 5 minutes, go to 45 acetonitrile in water in 5 minutes, remain at 46% acetonitrile in water for 20 minutes, and then go to 60% acetonitrile in water in 5 minutes. The total duration of the program was 35 minutes with the phytohormone eluting at between about 17 and about 18 minutes. For the fourth pass, the HPLC system was again programmed to supply 20% acetonitrile in water for the first 5 minutes, go to 40% acetonitrile in water in 25 minutes, remain at 40% acetonitrile in water for 20 minutes, and then go to 60% acetonitrile in water in 5 minutes. The total duration of the program was 45 minutes with the phytohormone eluting at about 30 minutes. The total yield is about 0.2 to 0.3 mg of phytohormone per liter of induced culture. The structure of the phytohormone was determined and verified by nuclear magnetic resonance and mass spectroscopy. BJ Nod-V (C18:1) was derived from strain USDAI10. BJ Nod-V (Ac, C18:1), BJ Nod-V (C16:0), BJ Nod-V (Ac, C16:0) and BJ Nod-V (C16:1) were derived from strain USDA135.

PROCEDURE II

Treatment of Legumes with the Phytohormone

Legumes were treated with the phytohormone in its crude state (i.e., the butanol extract from Procedure I,B hereinabove) and in its purified state (i.e., the phytohormone from Procedure I,D hereinabove). The phytohormone was effective at inducing several biological activities.

A. The induction of root hair curling: Dilutions from $10^{-3}$M to $10^{-12}$ of the phytohormone were added to hydroponically grown legume seedlings (soybean, *Glycine soja*, and siratro, *Macroptilium atropurpureum*). The root hairs of the seedlings were examined 24–96 hours after addition of the phytohormone. Parallel controls were run in which similar amounts of solvent, without the phytohormone, were added, as well as plants with no additions. Biological activity of the phytohormone were scored on a scale of 1 to 5 with 5 exhibiting marked deformations and swelling of the root hairs. Phytohormone activity was detectable, a grade of 3 or higher on the scale, down to a concentration of at least $10^{-12}$M. At concentrations of greater than about $10^{-3}$M, the phytohormone exhibited an inhibitory effect with respect to root hair curling.

B. The induction of flavonoids: Dilutions from $10^{-3}$M to $10^{-12}$M of the phytohormone were added to soybean seedlings grown hydroponically. Samples of the growth medium were removed between 4 and 12 days after addition of the phytohormone. The medium samples were then tested for their ability to induce a nodY-lacZ fusion in *B. japonicum*, strain USDA135. The phytohormone induced the production of flavonoids in the treated plants. High levels of the phytohormone inhibit flavonoid production.

C. The induction of cortical cell division: At the end of the incubation period for each of the above tests, the plants were removed and the roots were sectioned by hand. The roots were examined for the presence of foci of root cell division in accordance with N. Deshmane and G. Stacey, *J. of Bacteriology*, 171 (1989), pp. 3324–3330. Small nodule-like structures equivalent in number and size to foci on like roots grown in a like medium for a like time period, formed on the treated roots within 9–12 days of the addition of the phytohormone. This is a similar time scale as the formation of bacterium-induced nodulation. The activity of the phytohormone was detectable down to a concentration of at least $10^{-12}$M. At concentrations of greater than about $10^{-3}$M, the phytohormone exhibited an inhibitory effect on the plants with respect to cortical cell division.

Thus, the present invention provides a phytohormone for inducing root hair curling and nodulation in leguminous plants. This induction is accomplished in the absence of nitrogen-fixing bacteria.

Various of the features of the invention which are believed to be new are set forth in the appended claims.

What is claimed is:

1. A phytohormone for inducing root hair curling and root nodulation in the roots of leguminous plants, said phytohormone is a 6-α-2-O-methylfucose pentasaccharide having the structure:

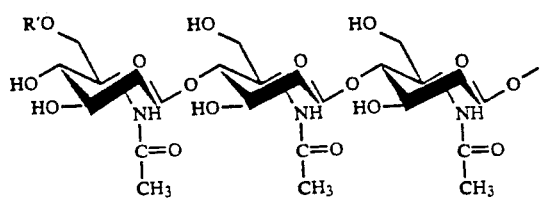

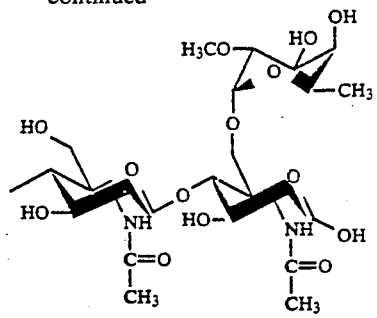

wherein R is selected from the group consisting of $(CH_2)_{15}CH_3$ and $(CH_2)_n—CH=CH—(CH_2)_m—CH_3$, wherein n+m is 13 or 15 and R' is selected from the group consisting of H and $CH_3CH_2C=O$.

2. A method for treating the roots of leguminous plants for inducing root hair curling and root nodulation, said method comprising treating the roots of the plants with a 6-α-2-O-methylfucose pentasaccharide having the structure:

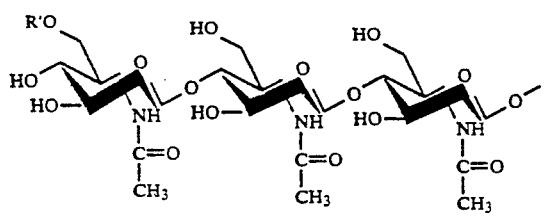

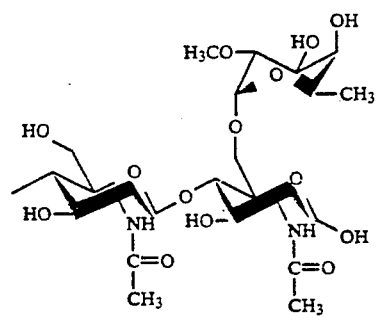

wherein R is selected from the group consisting of $(CH_2)_{15}CH_3$ and $(CH_2)_n—CH=CH—(CH_2)_m—CH_3$, wherein n+m is 13 or 15 and R' is selected from the group consisting of H and $CH_3CH_2C=O$.

3. The method of claim 2 wherein the roots of the plants are treated with said 6-α-2-O-methylfucose pentasaccharide at a concentration of from about $10^{-12}$M to about $10^{-3}$M.

4. The method of claim 2 wherein said roots are treated with said 6-α-2-O-methylfucose pentasaccharide in the absence of nitrogen fixing bacteria.

5. The method of claim 4 wherein said treated roots exhibit foci of root cell division equivalent to roots of like plants grown in the presence of nitrogen-fixing bacteria but without the addition of said 6-α-2-O-methylfucose pentasaccharide to said roots of said like plants.

6. The method of claim 2 wherein said 6-α-2-O-methylfucose pentasaccharide induces the production of flavonoids by said plants.

* * * * *

UNITED STATES PATENT AND TRADEMARK OFFICE
CERTIFICATE OF CORRECTION

PATENT NO. : 5,321,011
DATED : June 14, 1994
INVENTOR(S) : Gary Stacey, Russell W. Carleson, Herman Spaink It is certified that error appears in the above-identified patent and that said Letters Patent is hereby corrected as shown below:

<u>Column 4, Line 48</u>

Delete "USDAI10" and insert --USDA 110--.

Signed and Sealed this

First Day of November, 1994

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO : 5,321,011

DATED : June 14, 1994

INVENTOR(S): Stacey et al.

It is certified that error appears in the above-identified patent and that said Letters Patent are hereby corrected as shown below:

Column 2, lines 10-30, in the phytohormone structure, delete the terminal "$CH_3$" group located at the end of the bond line leading from the "C=O" connected through the "NH" to the first or leftmost acetylyglucosamine unit and replace the "$CH_3$" group at that site with --R-- so that the resulting phytohormone structure corresponds to the phytohormone structure of Fig. 1.

Column 4, line 32, after "45" and before "acetonitrile", insert "%".

Column 5, line 59 - column 6, line 13, in the phytohormone structure, delete the terminal "$CH_3$" group located at the end of the bond line leading from the "C=O" connected through the "NH" to the first or leftmost acetylyglucosamine unit and replace the "$CH_3$" group at that site with --R-- so that the resulting phytohormone structure corresponds to the phytohormone structure of Fig. 1.

UNITED STATES PATENT AND TRADEMARK OFFICE
CERTIFICATE OF CORRECTION

PATENT NO : 5,321,011
DATED : April 15, 1999
INVENTOR(S): Stacey et al.

It is certified that error appears in the above-identified patent and that said Letters Patent are hereby corrected as shown below:

Column 6, lines 25-45, in the phytohormone structure, delete the terminal "$CH_3$" group located at the end of the bond line leading from the "C=O" connected through the "NH" to the first or leftmost acetylyglucosamine unit and replace the "$CH_3$" group at that site with --R-- so that the resulting phytohormone structure corresponds to the phytohormone structure of Fig. 1.

Signed and Sealed this

Fourteenth Day of December, 1999

Q. TODD DICKINSON

Attest:

Attesting Officer

Acting Commissioner of Patents and Trademarks

UNITED STATES PATENT AND TRADEMARK OFFICE
CERTIFICATE OF CORRECTION

PATENT NO. : 5,321,011 Page 1 of 1
APPLICATION NO. : 07/822925
DATED : June 14, 1994
INVENTOR(S) : Gary Stacey et al.

It is certified that error appears in the above-identified patent and that said Letters Patent is hereby corrected as shown below:

On the Title page, (*) notice the Notice should read as follows:
-- [*] Notice: The portion of the term of this patent subsequent to Oct. 4, 2011 has been disclaimed. --

Signed and Sealed this

Seventh Day of November, 2006

JON W. DUDAS
*Director of the United States Patent and Trademark Office*